United States Patent [19]

Katoh et al.

[11] Patent Number: 5,302,743
[45] Date of Patent: Apr. 12, 1994

[54] PREPARATION OF N-PROTECTED α-L-ASPARTYL-L-PHENYLALANINE METHYL ESTER

[75] Inventors: Toshio Katoh, Kawasaki; Chojiro Higuchi, Kamakura; Takeshi Oura, Zushi; Masanobu Ajioka, Yokohama; Akihiro Yamaguchi, Kamakura, all of Japan

[73] Assignee: Mitsui Toatsu Chemicals, Inc., Tokyo, Japan

[21] Appl. No.: 823,538

[22] Filed: Jan. 21, 1992

Related U.S. Application Data

[63] Continuation-in-part of Ser. No. 639,768, Jan. 14, 1991, abandoned, which is a continuation of Ser. No. 327,230, Mar. 22, 1989, abandoned.

[30] Foreign Application Priority Data

| | | | |
|---|---|---|---|
| Mar. 22, 1988 | [JP] | Japan | 63-65920 |
| May 9, 1988 | [JP] | Japan | 63-110403 |
| May 9, 1988 | [JP] | Japan | 63-110417 |
| Jun. 13, 1988 | [JP] | Japan | 63-143674 |
| Jul. 1, 1988 | [JP] | Japan | 63-162593 |
| Jul. 7, 1988 | [JP] | Japan | 63-169782 |
| Jul. 7, 1988 | [JP] | Japan | 63-169783 |
| Jul. 21, 1988 | [JP] | Japan | 63-180358 |

[51] Int. Cl.$^5$ .................................... C07C 229/00
[52] U.S. Cl. ............................. 560/49; 560/41; 560/38
[58] Field of Search ................... 560/41, 38, 49

[56] References Cited

U.S. PATENT DOCUMENTS

| | | | |
|---|---|---|---|
| 3,872,110 | 3/1975 | Ariyoshi et al. | 549/253 |
| 4,680,403 | 7/1987 | Hisamitsu et al. | 560/38 |

FOREIGN PATENT DOCUMENTS

2140805 12/1984 United Kingdom ............... 560/34

Primary Examiner—José G. Dees
Assistant Examiner—Keith MacMillan
Attorney, Agent, or Firm—Millen, White, Zelano & Branigan

[57] ABSTRACT

Disclosed is an improved process for the preparation of an N-protected α-L-aspartyl-L-phenylalanine methyl ester from an N-protected L-aspartic anhydride and L-phenylalanine methyl ester, the improvement which comprises employing the L-phenylalanine methyl ester in the form of a mineral acid salt thereof and conducting the reaction either (a) in an organic solvent and in the presence of a salt of an organic carboxylic acid, or (b) in an organic solvent comprising an organic carboxylic acid and in the presence of at least one member of the group consisting of an alkali metal or an alkaline earth metal inorganic base, an ammonium alkali metal or alkaline earth metal salt of an organic carboxylic acid and ammonium carbonate. The starting N-protected aspartic anhydride, e.g., N-benzyloxycarbonyl-L-aspartic anhydride, can be produced by the reaction of N-protected aspartic acid with phosgene. When the N-protecting group sibenzyloxycarbonyl and the solvent is acetic acid, the desired product can be isolated from the reaction mixture in crystalline form in high purity by adding water thereto.

20 Claims, No Drawings

PREPARATION OF N-PROTECTED α-L-ASPARTYL-L-PHENYLALANINE METHYL ESTER

CROSS-REFERENCE TO RELATED APPLICATIONS

This application is a continuation-in-part application of U.S. application Ser. No. 07/639,768, filed Jan. 14, 1991, now abandoned, which is a continuation of U.S. application Ser. No. 07/327,230, filed Mar, 22, 1989, now abandoned.

BACKGROUND OF THE INVENTION a) Field of the Invention

The present invention relates to a process for the preparation of an N-protected α-L-aspartyl-L-phenylalanine methyl ester, which is an important intermediate compound for preparing α-L-aspartyl-L-phenylalanine methyl ester, which has sweetness of good quality and a sweetness degree of about 200 times the sweetness of sucrose. Therefore, its use as a diet sweetener is continuing to expand.

In the process of this invention, the N-protected α-L-aspartyl-L-phenylalanine methyl ester is prepared by the reaction of an N-protected L-aspartic anhydride with an acid addition salt of L-phenylalanine methyl ester in an organic solvent and in the presence either of a salt of an organic carboxylic acid or, when the organic solvent comprises an organic carboxylic acid, in the presence of an inorganic alkali metal or alkaline earth metal organic base, an ammonium alkali metal or alkaline earth metal salt of an organic carboxylic acid or ammonium carbonate.

The use of an acid addition salt rather than the free base form is critical for the prevention of self-cyclization reaction of the free amine in L-phenylalanine methyl ester and the ring cleaving reaction of the N-protected L-aspartic anhydride by water.

The process of the present invention lacks the disadvantages of the prior art, i.e., it avoids the production of byproducts by cyclization such as diketopiperazine compounds and it suppresses the production of β-isomers, thereby improving the yield and purity of the end product. Moreover, when the reaction solvent comprises an organic carboxylic acid, the N-protected α-L-phenylalanine methyl ester can be selectively crystallized from the reaction mixture.

b) Description of the Prior Art

α-L-Aspartyl-L-phenylalanine methyl ester is a dipeptide compound composed of L-aspartic acid and L-phenylalanine methyl ester. Various methods have already been disclosed for the preparation of this compound and these methods are primarily chemical processes.

An N-protected L-aspartic anhydride is generally employed for the starting material. For example, in one known process, N-protected L-aspartic anhydride is subjected to a condensation reaction with L-phenylalanine methyl ester in an organic solvent and subsequently cleaving the protective group with a usual method to obtain α-L-aspartyl-L-phenylalanine methyl ester (U.S. Pat. No. 3,786,039).

In other processes, L-phenylalanine methyl ester is reacted with N-protected L-aspartic anhydride in an inert reaction medium. In accordance with the process of G.B. Application 708463, an ethyl acetate solution of N-benzyloxycarbonyl-L-aspartic anhydride and an ethyl acetate solution of L-phenylalanine methyl ester hydrochloride are mixed. A 1N aqueous sodium carbonate solution is added to the mixture to initiate the reaction by neutralizing the L-phenylalanine methyl ester hydrochloride salt.

In U.S. Pat. No. 4,824,994, L-phenylalanine methyl ester is reacted in a non-reactive solvent, e.g., toluene or toluene plus acetic acid, with N-carbobenzoxy-L-aspartic anhydride.

In a known process which does not use L-phenylalanine methyl ester, N-formyl-L-aspartic anhydride is subjected to a condensation reaction with L-phenylalanine in acetic acid and then the formyl group is removed in the presence of an aqueous hydrogen halide solution. The reaction product is subsequently esterified by treating with water, alcohol and the aqueous hydrogen halide solution, and α-L-aspartyl-L-phenylalanine methyl ester is isolated in the form of its hydrogen halide salt (U.S. Pat. No. 3,933,781).

A process for reacting N-benzyloxycarbonyl-L-aspartic anhydride with L-phenylalanine methyl ester in an inert organic solvent by reaction of the hydrochloride salt with a base is also known (Dahlmans et al., U.S. Pat. No. 3,808,190). For example, N-benzyloxycarbonyl-L-aspartic anhydride and L-phenyl-alanine methyl ester hydrochloride are dissolved in ethyl acetate and then an aqueous sodium carbonate or potassium carbonate solution is added to the resultant solution, which converts the hydrochloride acid addition salt of the L-phenyl-alanine methyl ester in situ into its free base form as evidenced by the disclosure in Dahlmans et al. at col. 2, lines 17-19, which states that the amount of base added is at least equivalent to the amount of the amino acid ester addition salt.

By adding a base at least equivalent to the amount of amino acid ester, the amino acid methyl ester acid addition salt is converted to its free base form, which is unstable and self-condensates to form a diketopiperidine. In fact, Dahlmans et al. disclose at col. 3, lines 13-15:

"the use of an aqueous solution of the base in the reaction of the present invention results in some racemization of the aspartyl-amino acid esters produced."

In contrast, the present invention is directed to the reaction of N-protected L-aspartic anhydride with a mineral acid addition salt of L-phenylalanine methyl ester and does not occur via the unstable free base form of L-phenylalanine methyl ester.

The reaction system of Dahlmans et al. contains an inert solvent, base and water. Although the inert solvent does not react with the reactants (see col. 4, lines 18-25), the base does and the adverse effect of using the free base form of the amino acid methyl ester inevitably occurs. In contrast, the reaction system of the present invention employs the stable form (acid addition salt) of the amino acid methyl ester. When the reaction of this invention is conducted in the presence of a base, the reaction solvent also includes an organic carboxylic acid, which is not merely an inert solvent because it prevents the formation of the unstable free base form of the amino acid methyl ester. Furthermore, no water is employed in applicants' reaction system, in contradistinction to Dahlmans et al. (col. 2, lines 22-24).

Takahashi et al. (U.S. Pat. No. 4,824,994) is directed to the production of N-carbobenzoxy alpha-L-aspartyl-L-phenylalanine methyl ester by reacting N-carbobenzoxy L-aspartic anhydride with L-phenylalanine methyl ester in its unstable free base form. The distinguishing feature of that process is the particle diameter of N-carbobenzoxy L-aspartic anhydride which has a particle diameter of not more than 130 μm. Takahashi et al. discovered that the smaller the particle diameter, the higher the ratio of the α to β isomers of N-carbobenzoxy alpha-L-aspartyl-L-phenyl-alanine methyl ester which is produced.

Takahashi et al. disclose at col. 2, lines 49–52, that the solvent is used merely for suspending the reactants. Although acetic acid is disclosed as an illustration of such an inert solvent, the acetic acid in Takahashi et al. is used merely as a suspending agent. Thus, as in Dahlmans et al., the amino acid ester is used in Takahashi et al. in a free base form, which is unstable under conventional conditions and which results in less than optimum yield and purity of the desired product.

Tertiary amines are also used in U.S. Pat. No. 3,808,190 as a base for promoting the reaction, in which case the reaction is carried out in the organic solvent by neutralizing the hydrochloride salt of L-phenylalanine methyl ester with an aqueous alkali solution. The inevitable disadvantage is that the ester group of L-phenylalanine methyl ester is hydrolyzed by the aqueous alkali solution, diketopiperazine compounds are formed as by-products by cyclization under alkaline conditions or basic conditions due to tertiary amines, in particular, and water causes ring-cleavage reaction of N-protected L-aspartic anhydride.

On the other hand, a process for conducting the reaction of N-formyl-L-aspartic anhydride with L-phenylalanine methyl ester in a solvent in the presence of acetic acid or formic acid is also known (EP 227301).

In U.S. Pat. No. 4,680,403, N-benzyloxycarbonyl-L-aspartic acid is converted to its anhydride in toluene with acetic anhydride and then reacted with L-phenylalanine methyl ester by the addition of a toluene solution thereof.

The L-phenylalanine methyl ester used as a raw material in these processes is usually obtained by reacting L-phenylalanine with methanol and a mineral acid such as hydrogen chloride, followed by neutralizing the resultant mineral acid salt of L-phenylalanine methyl ester.

However, the free amine form of L-phenylalanine methyl ester is thermally unstable and readily dimerized into diketopiperazine derivatives under conditions around neutrality, in particular, where neutralization and extraction operations are carried out. Additional limitations are placed on the yields of neutralization and extraction, and hence there is a disadvantage that the overall yield decreases on the basis of expensive L-phenylalanine.

OBJECTS OF THE INVENTION

It is an object of this invention to eliminate the various drawbacks of conventional processes set forth about and to provide an industrially outstanding process for the preparation of an N-protected α-L-aspartyl-L-phenylalanine methyl ester.

Another object of this invention is to provide a process for selectively crystallizing N-benzyloxycarbonyl-α-L-aspartyl-L-phenylalanine methyl ester from the reaction product obtained by reacting N-benzyloxycarbonyl-L-aspartic anhydride with a mineral acid salt of L-phenylalanine methyl ester in an organic carboxylic acid, by the addition of water thereto.

Still another object of this invention is to provide a process for the preparation of an N-protected α-L-aspartyl-L-phenylalanine methyl ester by converting an N-protected L-aspartic acid to its anhydride and then reacting the anhydride with a mineral acid salt of L-phenylalanine methyl ester.

A further object of this invention is to provide a process for preparing an N-protected α-L-aspartyl-L-phenylalanine methyl ester using an N-protected L-aspartic anhydride obtained by reacting an N-protected aspartic acid with acetic anhydride or phosgene.

Other objects will be apparent to those skilled in the art to which this invention pertains.

SUMMARY OF THE INVENTION

In one aspect, this invention relates to a process for the preparation of an N-protected α-L-aspartyl-L-phenylalanine methyl ester comprising reacting an N-protected L-aspartic anhydride with a mineral acid salt of L-phenylalanine methyl ester, either (a) as a nonaqueous inert organic solvent and in the presence of a salt of an organic carboxylic acid, or (b) in a nonaqueous organic solvent comprising an organic carboxylic acid and in the presence of alkali metal or an alkaline earth metal inorganic base, an ammonium, alkali metal or an alkaline earth metal salt of an organic carboxylic and ammonium carbonate.

In another aspect, this invention relates to a process for preparing N-benzyloxycarbonyl-α-L-aspartyl-L-phenylalanine methyl ester by use of benzyloxycarbonyl group for the N-protecting group which comprises adding water after completion of the above reaction in which the reaction solvent is an organic carboxylic acid to selectively crystallize N-benzyloxycarbonyl-α-L-aspartyl-L-phenylalanine methyl ester from the reaction mixture.

In a further aspect, this invention relates to a process for the preparation of the N-protected α-L-aspartyl-L-phenylalanine methyl ester by first reacting an N-protected L-aspartic acid with acetic anhydride in the organic carboxylic acid and then employing the resultant N-protected L-aspartic anhydride as the starting material for the reaction without isolation from the reaction mixture.

DETAILED DESCRIPTION OF THE INVENTION

The present inventors have intensively carried out an investigation on the reaction of N-protected L-aspartic anhydride with L-phenylalanine methyl ester in order to provide a satisfactory process for industrial production.

In conventional processes for reacting an N-protected L-aspartic anhydride with L-phenylalanine methyl ester, L-phenylalanine methyl ester is isolated by subjecting its mineral acid salt to a treatment such as neutralization, extraction and dehydration.

The present inventors have found a novel process for the preparation of an N-protected α-L-aspartyl-L-phenylalanine methyl ester without isolating L-phenylalanine methyl ester by subjecting a mineral acid salt of L-phenylalanine methyl ester to a condensation reaction with an N-protected L-aspartic anhydride in the presence of (a) an organic solvent and a salt of an organic carboxylic acid or (b) an organic carboxylic acid and at least one member of the group consisting of an inorganic base of an alkali metal compound or an alkaline earth metal compound, a salt of an organic carboxylic acid of an alkali metal or an alkaline earth metal, ammonium carbonate, and an ammonium salt of an organic carboxylic acid.

The inventors have also found that, when benzyloxycarbonyl group is used for the protection of amine, N-benzyloxycarbonyl-α-L-aspartyl-L-phenylalanine methyl ester can be selectively crystallized by the addition of water to the reaction system after completing the above reaction.

In a process of this invention, the mineral acid salt of L-phenylalanine methyl ester in an organic solvent is reacted substantially in the form of L-phenylalanine methyl ester by adding a salt of the organic carboxylic acid thereto or by the addition to a solution of the methyl ester in an organic carboxylic acid, of at least one member of the group consisting of an inorganic base of an alkali metal compound or an alkaline earth metal compound, a salt of an organic carboxylic acid and an alkali metal or an alkaline earth metal, ammonium carbonate and an ammonium salt of an organic carboxylic acid. It is an advantage of the process that in the presence of the organic carboxylic acid, self-cyclization reaction of free amine in L-phenylalanine methyl ester and the ring cleaving reaction of the N-protected L-aspartic anhydride by water does not take place at all. N-Protected α-L-aspartyl-L-phenylalanine methyl ester can thus be prepared in good yield and purity.

Exemplary N-protecting groups which can be used in the process of this invention include acyl groups such as benzyl, acetyl, formyl, halogenated acetyl, trifluoroacetyl and trichloroacetyl, triphenylmethyl group; sulfonyl groups such as p-toluenesulfonyl; alkoxybenzyloxycarbonyl groups such as p-methoxybenzyloxycarbonyl; halogenobenzyloxycarbonyl groups such as p-chlorobenzyloxycarbonyl; and substituted or unsubstituted benzyloxycarbonyl groups such as p-nitrobenzyloxycarbonyl. Preferred are formyl, trifluoroacetyl and benzyloxycarbonyl. When benzyloxycarbonyl is used as the protecting group for the amino group, the protecting group can readily be removed by catalytic reduction. Thus there is no problem of hydrolysis of the methyl ester group which is favorable for carrying out removal of the protecting group in high selectivity.

These N-protected L-aspartic anhydrides can be prepared by various methods and known methods described below are employed.

For example, N-formyl-L-aspartic anhydride can readily be prepared by reacting L-aspartic acid with formic acid in acetic anhydride (GB 708463).

N-Trifluoroacetyl-L-aspartic anhydride can be prepared by gradually adding trifluoroacetic anhydride to previously cooled L-aspartic acid. N-Acetyl-L-aspartic anhydride and N-trichloroacetyl-L-aspartic anhydride can also be synthesized in accordance with the above process [J. Med. Chem. 11, 163 (1973)].

N-Benzyloxycarbonyl-1-aspartic anhydride can be obtained by reacting L-aspartic acid with carbobenzoxy chloride and then further reacting the resultant N-benzyloxycarbonyl L-aspartic acid with a dehydrating agent, for example, acetic anhydride.

It is, however, necessary to use a chemical excess of acetic anhydride in order to optimize the yield of N-protected L-aspartic anhydride. It is also industrially favorable to employ N-protected L-aspartic anhydride thus obtained for the next step in the form of the intact solution. However, residual acetic anhydride in the reaction mixture often causes side reactions. For example, when the solution of N-formyl-L-aspartic anhydride in acetic anhydride obtained above is reacted with L-phenylalanine methyl ester to prepare N-formyl-α-L-aspartyl-L-phenylalanine methyl ester, it is undesirable that acetic anhydride remain in the solution as it causes acetylation of L-phenylalanine methyl ester.

Although N-protected L-aspartic anhydride can also be used after isolation (U.S. Pat. No. 3,808,190), removal of excess acetic anhydride and the thus-formed acetic acid is difficult and racemization of aspartic acid is apt to occur during the isolating operation at high temperatures.

In order to eliminate these disadvantages, the present inventors have carried out an intensive investigation on the process for preparing N-protected L-aspartic anhydride without the use of acetic anhydride. As a result, it has been found that N-protected L-aspartic anhydride can be prepared in good yield and purity by the reaction of N-protected L-aspartic acid with phosgene in an inert organic solvent.

A preferred aspect of the present invention is a process for the preparation of an N-protected α-L-aspartyl-L-phenylalanine methyl ester which comprises using an N-protected L-aspartic anhydride obtained by reacting N-protected L-aspartic acid with phosgene in the organic solvent in the presence or absence of an oxide, hydroxide or a salt of any of a variety of metals, including alkali metals, alkaline earth metals and transition metals.

Some N-protecting groups generally employed are eliminated in acidic conditions and hence it was assumed that by-products having an unprotected amino group result from the action of hydrogen chloride generated as a by-product by the reaction of N-protected L-aspartic anhydride with phosgene. However, unexpectedly, it has been found that this side reaction scarcely occurs under the conditions of this invention.

The organic solvent employed in this step of this invention is inert in the reaction and inactive to phosgene, in particular. Exemplary organic solvent includes ethers such as ethyl ether, butyl ether, tetrahydrofuran and dioxane; halogenated hydrocarbons such as chloroform, dichloromethane, carbon tetrachloride, 1,2-dichloroethane, 1,1,2-trichloroethane, and chlorobenzene; hydrocarbons such as n-hexane, cyclohexane, benzene and toluene; and esters such as ethyl acetate and butyl acetate.

Addition of an oxide, hydroxide or salt of a metals (hereinafter referred to as the metal compound) is effective for decreasing to a large extent the reaction time of this invention. Suitable metal compound includes, for example, oxides and hydroxides of alkali metals such as lithium, sodium and potassium; alkali earth metals such as magnesium and calcium, transition metals such as iron, copper and zinc; miscellaneous metals such as tin and aluminum; and salts of these metals with various acids such as chloride, sulfate, nitrate, carbonate, phosphate, acetate and carboxylate.

No restriction is placed, in particular, on the amount of the metal compound employed. The metal compound can be used in a broad range without adverse effect in the next step of the reaction. The metal compound is usually employed in the amount of from about 0.001 mol % to about 5 mol % per mol of N-protected aspartic acid.

The metal compound is generally added to the reaction mixture at the initiation or in the course of the reaction, and exhibits a satisfactory effect both in the dissolved state and in the suspended state.

The reaction is carried out by dissolving or suspending an N-protected-L-aspartic acid in the above organic solvent and then by adding phosgene with stirring, if necessary, in the presence or absence of the metal compound. Phosgene is usually used in a molar excess in order to remove generated hydrogen chloride and carbon dioxide from the reaction system. The reaction temperature is preferably in the range of from −10° C. to 90° C. and more preferably from 10° C. to 60° C. When the temperature is higher than this range, side reactions such as racemization and cleavage of the protecting group are liable to take place. On the other hand, temperatures lower than this range results in longer reaction time, which is impractical from an economics point of view.

After finishing the reaction, excess phosgene is removed and precipitated crystals of the desired product are filtered as is and dried. When the desired product is dissolved, the reaction mixture is merely concentrated. Thus an N-protected L-aspartic anhydride can readily be obtained. The intact reaction mixture can also be used for the next step by merely eliminating residual phosgene. Consequently, formation of by-products can be inhibited and the reaction step can be simplified, which is very effective for the industrial production of α-L-aspartyl-L-phenylalanine methyl ester.

Various methods have also been known for preparing the N-benzyloxycarbonyl-L-aspartic anhydride having a particularly suitable protecting group employed in this invention.

For example, N-benzyloxycarbonyl-L-aspartic acid is dissolved in a large excess of acetic anhydride, the acetic acid formed by the reaction and the excess acetic anhydride are distilled off under reduced pressure and the effect of any acetic acid remaining in the residue is removed by the addition of an organic solvent to give N-benzyloxycarbonyl-L-aspartic anhydride [J. Am. Chem. Soc., 81, 167–173 (1959)].

In another process, N-benzyloxycarbonyl-L-aspartic acid is slurried in acetic anhydride, reacted at a temperature of 50° C. or less, then cooled, followed by adding a mixture of ether and petroleum ether to separate the desired product (GB Appln. 708,463). Alternatively. N-benzyloxycarbonyl-L-aspartic acid is reacted with acetic anhydride in the presence of an aromatic hydrocarbon (Japanese Patent Laid-Open No. 75542/1973).

However, in any of the processes set forth above, use of acetic anhydride in large excess is uneconomical. Further, excess acetic anhydride and resultant acetic acid must be distilled off in order to isolate the desired product, thereby causing complex operation. Addition of the organic solvent having a low flash point is also unsatisfactory for industrial application.

In the industrial production of an N-protected L-aspartyl-L-phenylalanine methyl ester, it is generally desired from the stand point of operation convenience to carry out the condensation reaction of the N-protected L-aspartic anhydride and the L-phenylalanine methyl ester without isolating the anhydride of precursor.

However, when the reaction is conducted using excess acetic anhydride as the dehydrating agent, by-products are formed in the subsequent condensation with L-phenylalanine methyl ester. Consequently, the yield of desired anhydride is enhanced by using a minimum amount of acetic anhydride.

Japanese Patent Laid-Open No. 167577/1983 discloses a method for carrying out the reaction of N-benzyloxycarbonyl-L-aspartic acid with acetic anhydride in the presence of an oxide, hydroxide or salt of various metals or of an organic base.

The method also employs organic solvent to lower the amount of acetic anhydride used and is effective for reducing the reaction time. In the industrial application of the method, however, a problem of acetic acid separation in the recovery of the organic solvent exists.

The present inventors have carried out an intensive investigation on the preparation of N-benzyloxycarbonyl-L-aspartic anhydride in order to remove the disadvantages of conventional processes as set forth above and to obtain the desired product, N-benzoyloxycarbonyl-L-aspartic anhydride, in high yield within a short period of time. Consequently, it has been found that the reaction rate of aspartic acid dehydration is remarkably increased by conducting the reaction in the presence of an acid halide or phosphorus halide and the desired N-benzyloxycarbonyl-L-aspartic anhydride can be obtained in high yield within a short period of time.

Accordingly, in one aspect of the present invention relates to a process for preparing N-benzyloxycarbonyl-L-aspartyl-L-phenylalanine methyl ester which comprises using the N-benzyloxycarbonyl-L-aspartic anhydride obtained by the reaction of N-benzyloxycarbonyl-L-aspartic acid with acetic anhydride in an organic carboxylic acid in the presence of an acid halide or a phosphorus halide.

Preferred acid halides used in this aspect of the process of this invention include, for example, carboxylic acid chlorides such as acetyl chloride, pivaloyl chloride, lauroyl chloride, benzoyl chloride and chloroacetyl chloride; acid bromides such as acetyl bromide and bromoacetyl bromide; acid iodides such as acetyl iodide; sulfur acid chlorides such as thionyl chloride and sulfuryl chloride; sulfonic acid halides such as benzensulfonyl chloride and p-toluenesulfonyl chloride; sulfinic acid halides; and phosphoric acid halides such as phosphoryl trichloride. Preferred phosphorus halides include phosphorus trihalides such as phosphorus trichloride, phosphorus tribromide and phosphorus triiodide; and phosphorus pentahalides such as phosphorus pentachloride and phosphorus pentabromide.

The amount of the halide used in the reaction varies somewhat depending upon the type of the halide added. However, the presence of only a trace amount of the halide is satisfactory and has no adverse effect in the subsequent steps. That is, the presence in the trace amount exhibits a catalytically effective action. Suitable amount of the halide compound for the industrial production is in the range of from about $1 \times 10^{-5}$ to about $5 \times 10^{-3}$ by weight per weight of N-benzyloxycarbonyl-L-aspartic acid.

Any type of solvent can be used in the process of this invention so long as the solvent is inactive to the reactants and products in the reaction. Representative examples of suitable solvents include ketones such as acetone and methyl ethyl ketone; ethers such as diethyl ether, tetrahydrofuran and dioxane; nitrides such as acetonitrile; esters such as ethyl acetate and methyl propionate; carboxylic acids such as formic acid, acetic acid and propionic acid; halogenated hydrocarbons such as chloroform, dichloromethane and ethylenedichloride; hydrocarbons such as toluene, xylene, hexane and cyclohexane; amides such as dimethylformamide; and other miscellaneous solvents such as dimethylsulfoxide, γ-butyrolactone and nitromethane. These solvents can be used singly or in combination as a mixture.

Acetic acid is a preferred solvent in view of solvent recovery, because no solvent separation operation is needed for separating it from the acetic acid generated in the reaction.

The amount of acetic anhydride used in the process is preferably from 0.5 mole to 2 moles and more preferably from 0.9 mole to 1.05 moles per mole of N-benzyloxycarbonyl-L-aspartic acid. The range of reaction temperature is generally from −10° C. to 100° C. and preferably from 0° C. to 80° C. for inhibiting the production of product resulting from racemization.

Since the process is preferably carried out using only a small chemical excess amount of acetic anhydride, recovery of the residual acetic anhydride is unnecessary. When acetic acid is used as the solvent, the resultant N-benzyloxycarbonyl-L-aspartic anhydride is preferably used without isolation from the reaction mixture, for the reaction with L-phenylalanine methyl ester. In this case, there are no adverse effects on the reaction and, moreover, formation of by-products can be inhibited and the production steps can be simplified. Accordingly, the process is extremely effective for the industrial production of N-benzyloxycarbonyl-α-L-aspartyl-L-phenylalanine methyl ester.

The organic solvents used for the reaction of N-protected L-aspartic anhydride with the mineral acid salt of L-phenylalanine methyl ester are inactive to the N-protected L-aspartic anhydride. Aliphatic halogenated hydrocarbon solvents, fatty acid ester solvents and hydrocarbon solvents are preferred.

Exemplary suitable solvents include aliphatic halogenated hydrocarbon solvents such as methylene chloride, ethylene chloride, trichloroethylene and tetrachloro ethylene; fatty acid ester solvents such as ethyl acetate, butyl acetate, ethyl formate, propyl formate, methyl propionate and ethyl propionate; phosphoric acid ester solvents such as triethyl phosphate and tri-n-butyl phosphate; hydrocarbon solvents such as toluene, xylene and hexane; and ether solvents such as tetrahydrofuran and dioxane.

Suitable examples of the organic carboxylic acid used for the reaction of N-protected L-aspartic anhydride with the mineral acid salt of L-phenylalanine methyl ester include carboxylic acids, e.g., lower fatty acids such as formic acid, acetic acid and propionic acid. Preferred acids are acetic acid and propionic acid.

No limitation is imposed on the amounts of the organic solvent and organic carboxylic acid employed. The amount is usually from 2 to 50 times the weight of the raw material N-protected L-aspartic anhydride, depending on industrial operation conditions.

Any type of salt of all organic carboxylic acid can be used for the reaction of N-protected L-aspartic anhydride with the mineral acid salt of L-phenylalanine methyl ester so long as the salt is a salt of an organic carboxylic acid and a metal, such as an alkali metal or alkaline earth metal, or a corresponding ammonium salt. Exemplary suitable salt of the organic carboxylic acid includes lithium acetate, sodium acetate, potassium acetate, ammonium acetate, calcium acetate, magnesium acetate and barium acetate. Preferred salt is sodium acetate and potassium acetate.

Exemplary suitable inorganic base of alkali metal compounds or alkaline earth metal compounds which can be used in the reaction of N-protected L-aspartic anhydride with the mineral acid salt of L-phenylalanine methyl ester include a hydroxide, oxide, carbonate, hydrogen carbonate, hydrogenphosphate and dihydrogenphosphate of an alkali metal or an alkaline earth metl.

Exemplary suitable hydroxides of an alkali metal and alkaline earth metal includes sodium hydroxide, potassium hydroxide, lithium hydroxide and magnesium hydroxide. Exemplary suitable oxide of alkali metal and alkaline earth metal includes calcium oxide and magnesium oxide. Exemplary suitable carbonates of an alkali metal and alkaline earth metal includes lithium carbonate, sodium carbonate, potassium carbonate, calcium carbonate and magnesium carbonate. Exemplary suitable hydrogen carbonates of an alkali metal or an alkaline earth metal include lithium hydrogen carbonate, sodium hydrogen carbonate, potassium hydrogen carbonate and calcium hydrogen carbonate. Exemplary suitable organic carboxylic acid salts of an alkali metal and alkaline earth metal includes lithium acetate, sodium acetate, potassium acetate, calcium acetate and magnesium acetate. Preferred salts are sodium acetate and potassium acetate. Ammonium carbonate or an ammonium salt of the organic carboxylic acid can also be used.

An equimolecular amount of the salt of the organic carboxylic acid; of the hydroxide, oxide, carbonate, hydrogen carbonate of the alkali metal or alkaline earth metal, or salt of the organic carboxylic acid of alkali metal or alkaline earth metal; ammonium carbonate or ammonium salt of the organic carboxylic acid is sufficient to the mineral acid salt of L-phenylalanine methyl ester. These substances are usually used in an amount ranging from 1.0 mole to 3.0 moles per mole of the mineral acid salt of L-phenylalanine methyl ester.

In a preferred method for carrying out this aspect of the process of this invention, an N-protected L-aspartic anhydride is suspended or dissolved in the organic solvent, the salt of the organic carboxylic acid is added and then the mineral acid salt of L-phenylalanine methyl ester is added to the reaction mixture. Alter natively, the salt of the organic carboxylic acid is added after the addition of the mineral acid salt of L-phenylalanine methyl ester.

Any suitable reaction temperature can be employed in this aspect of this invention. The reaction temperature is usually in the range of from −15° C. to 50° C. and preferably in the range of from 5° C. to 25° C.

A reaction time sufficient to complete the reaction is usually from 0.5 hour to 10 hours.

In another method for carrying out the process of this invention, an N-protected L-aspartic anhydride is suspended or dissolved in the organic carboxylic acid, and then at least one member of the group consisting of an inorganic base of an alkali metal compound or an alkaline earth metal compound, a salt of an organic carboxylic acid of an alkali metal or an alkaline earth metal, ammonium carbonate and an ammonium salt of an organic carboxylic acid, is added to the resultant mixture, followed by the addition of the mineral acid salt of L-phenylalanine methyl ester. Alternatively, the mineral acid salt of L-phenylalanine methyl ester is added to the resultant mixture prior to the addition of at least one member of the group consisting of an inorganic base of an alkali metal compound or an alkaline earth metal compound, a salt of an organic carboxylic acid and an alkali metal or an alkaline earth metal, ammonium carbonate and an ammonium salt of an organic carboxylic acid.

Here also, any convenient reaction temperature can be employed in this aspect of this invention. The reaction temperature is usually in the range of from −15° C. to 80° C. and preferably in the range of from −5° C. to 25° C.

A reaction time sufficient to complete the reaction is usually from 0.5 hour to 10 hours.

In any of the methods set forth above, an N-protected α-aspartyl-L-phenylalanine methyl ester is generally precipitated from the reaction system after the reaction is finished. When an organic carboxylic acid is used as the solvent, the N-protected β-aspartyl-L-phenylalanine methyl ester formed as a by-product is relatively soluble in the organic carboxylic acid. Consequently, the desired N-protected α-aspartyl L-phenylalanine methyl ester can readily be isolated by the filtration and washing of the precipitated crystals thereof.

When the product is N-benzyloxycarbonyl-α-aspartyl-L-phenylalanine methyl ester, N-benzyloxycarbonyl-α-aspartyl-L-phenylalanine methyl ester can be selectively crystallized by the addition of water. The amount of water added is preferably selected so as to obtain an organic carboxylic acid concentration of from 5% to 90% by weight, preferably from 45% to 70% by weight.

When the acid concentration is less than 45% by weight, the purity of the N-benzyloxycarbonyl β-aspartyl-L-phenylalanine methyl ester is lowered. On the other hand, a concentration of more than 70% by weight lowers the yield of isolated N-benzyloxycarbonyl-α-aspartyl-L-phenylalanine methyl ester.

Any N-protected β-aspartyl-L-phenylalanine in the N-protected α-aspartyl-L-phenylalanine methyl ester thus isolated is present in a small amount and can readily be removed with water or an organic solvent according to the usual method.

In a still another method for carrying out a process of this invention, an N-protected L-aspartic acid is converted to its anhydride by reaction with acetic anhydride in an organic carboxylic acid as solvent. The resultant N-protected L-aspartic anhydride is obtained in a suspended or dissolved state in the reaction mixture. The alkali metal or alkaline earth metal hydroxide, oxide, carbonate or hydrogen carbonate or the salt of an organic carboxylic acid and an alkali metal or an alkaline earth metal; or ammonium carbonate, or an ammonium salt of an organic carboxylic acid is added to the reaction mixture, and then the mineral acid salt of L-phenylalanine methyl ester is added prior to carrying out the reaction. Alternatively, the mineral acid salt of L-phenylalanine methyl ester is first added to the reaction mixture and thereafter the alkali metal or the alkaline earth metal hydroxide, oxide, carbonate or hydrogen carbonate, or the salt of an organic carboxylic acid and an alkali metal or alkaline earth metal, or ammonium carbonate or an ammonium salt of an organic carboxylic acid is added prior to carrying out the reaction.

Conversion of N-protected L-aspartic acid to anhydride can be carried out in the temperature range of from 40° C. to 65° C., preferably in the range of from 50° C. to 60° C.

Any suitable reaction temperature can be employed for the reaction of the N-protected L-aspartic anhydride and L-phenylalanine methyl ester. The reaction temperature is usually in the range of from −50° C. to 80° C., and preferably ambient temperature or below, e.g., from −5° C. to 25° C.

The reaction time sufficient to complete the reaction is usually from 0.5 hour to 10 hours.

The same procedures as described above can be carried out in the post treatment of the reaction mixture.

In accordance with the process of this invention, an N-protected α-L-aspartyl-L-phenylalanine methyl ester, an important compound as an intermediate of α-L-aspartyl-L-phenylalanine methyl ester, can be effectively prepared under mild conditions within a short period of time.

The steps in the process of this invention can be simplified by combining them with the anhydride preparation step. Thus the process of this invention becomes valuable in view of industrial production.

The process of this invention will hereinafter be illustrated in detail by way of examples.

EXAMPLE

Example 1

In 100.1 g of ethyl acetate, 14.3 g (0.1 mole) of N-formyl-L-aspartic anhydride was suspended, and 9.2 g (0.11 mole) of sodium acetate was added at −50°–0° C. with stirring, and 21.6 g (0.1 mole) of L-phenylalanine methyl ester hydrochloride was further added at the same temperature. The mixture was reacted for 5 hours with stirring at the same temperature. Thereafter 14.3 g of acetic acid was added and stirred for an hour at the same temperature. Precipitated crystals were filtered, washed and dried. Crystals of N-formyl-α-L-aspartyl-L-phenylalanine methyl ester were obtained in a yield of 20.9 g (65.0% yield on L-phenylalanine methyl ester hydrochloride). The crystals obtained were analyzed by high performance liquid chromatography to give a ratio of α-isomer:β-isomer of 99.0:1.0.

Example 2

In 100.4 g of ethyl acetate 25.1 g (0.1 mole) of N-benzyloxycarbonyl-L-aspartic anhydride was suspended, and 9.2 g (0.11 mole) of sodium acetate was added at −5°–0° C. with stirring, and 21.6 g (0.1 mole) of L-phenylalanine methyl ester hydrochloride was added at the same temperature.

The mixture was reacted for 3 hours with stirring at the same temperature and concentrated under reduced pressure. Thereafter 100.4 g of acetic acid and 75.3 g of water were added and stirred for an hour at 15°–20° C. Precipitated crystals were filtered, washed and dried. Crystals of N-benzyloxycarbonyl-α-L-aspartyl-L-phenylalanine methyl ester were obtained in a yield of 29.1 g (68.0% yield on L-phenylalanine methyl ester hydrochloride). The crystals obtained were analyzed by high performance liquid chromatography to give a ratio of α-isomer:β-isomer of 99.3:0.7.

Example 3

In 84.4 g of ethyl acetate 21.1 g (0.1 mole) of N-trifluoroacetyl-L-aspartic anhydride was suspended, and 9.2 g (0.11 mole) of sodium acetate was added at −5 - 0° C. with stirring, and 21.6 g (0.1 mole) of L-phenylalanine methyl ester hydrochloride was added at the same temperature. The mixture was reacted for 3 hours with stirring at the same temperature and concentrated under reduced pressure. Thereafter 63.3 g of acetic acid was added and stirred for an hour at 15°–20° C. Precipitated crystals were filtered, washed and dried. Crystals of N-trifluoroacetyl-α-L-aspartyl-L-phenylalanine methyl ester were obtained in a yield of 30.6 g (78.5% yield on L-phenylalanine methyl ester hydrochloride). The crystals obtained were analyzed by high performance liquid chromatography to give a ratio of α-isomer:β-isomer of 99.0:1.0.

Example 4

In 179.4 g of methylenechloride, 14.3 g (0.1 mole) of N-formyl-L-aspartic anhydride was suspended, and 9.2 g (0.11 mole) of sodium acetate was added at 20°–25° C. with stirring, and 21.6 g (0.1 mole) of L-phenylalanine methyl ester hydrochloride was added at the same temperature during 30 minutes. The mixture was reacted for 5 hours with stirring at the same temperature. Precipitated crystals were filtered, washed and dried. Crystals of a mixture of N-formyl-α-L-aspartyl-L-phenylalanine methyl ester, and N-formyl-β-L-aspartyl-L-phenylalanine methyl ester were obtained in a yield of 30.0 g. The crystals obtained were analyzed by high performance liquid chromatography to give a ratio of α-isomer:β-isomer of 75.0:25.0. The crystals were purified by a conventional method to obtain pure crystals of N-formyl-α-L-aspartyl-L-phenylalanine methyl ester. The yield was 16.1 g (50% yield on L-phenylalanine methyl ester hydrochloride).

The results of elementary analysis were coincided with N-formyl-α-L-aspartyl-L-phenylalanine methyl ester.

| Elementary analysis (%) $C_{15}H_{18}N_2O_6$ | | | |
|---|---|---|---|
| | C | H | N |
| Found | 55.85 | 5.69 | 8.66 |
| Calculated | 55.90 | 5.63 | 8.69 |

Example 5

The same procedures as described in Example 4 were carried out except that the organic solvents illustrated in Table 1 were used. The results are shown in Table 1.

TABLE 1

| | | α-L-Aspartyl-L-phenylalanine methyl ester | |
|---|---|---|---|
| Experiment No. | Organic Solvent | Yield (%) | % Yield on L-phenylalanine methyl ester hydrochloride |
| 1 | Toluene | 16.1 | 50.0 |
| 2 | Ethylene chloride | 12.9 | 40.0 |
| 3 | Tri-n-butyl phosphate | 13.5 | 41.9 |
| 4 | 1,4-Dioxane | 17.7 | 55.0 |
| 5 | Butyl acetate | 18.4 | 57.1 |

Example 6

In 100 g of ethyl acetate, 14.3 g (0.1 mole) of N-formyl-L-aspartic anhydride and 21.6 g (0.1 mole) of L-phenylalanine methyl ester hydrochloride were suspended and 9.2 g (0.11 mole) of sodium acetate was added to the suspension during 30 minutes at 20°–25° C. with stirring. The mixture was reacted for 5 hours with stirring at the same temperature. Thereafter 14.3 g of acetic acid was added and stirred for an hour at the same temperature. Precipitated crystals were filtered, washed and dried. Crystals of N-formyl-α-L-aspartyl-L-phenylalanine methyl ester were obtained in a yield of 21.1 g (65.5% yield on L-Phenylalanine methyl ester hydrochloride). The crystals obtained were analyzed by high performance liquid chromatography to give a ratio of α-isomer:β-isomer of 98.0:2.0.

Example 7

The same procedures as described in Example 3 were carried out except that 27.7 g (0.1 mole) of L-phenylalanine methyl ester sulfate and 17.2 g (0.205 mole) of sodium acetate were used. The yield was 30.4 g (77.9% yield on L-phenylalanine methyl ester sulfate).

Example 8

The same procedures as described in Example 2 were carried out except that 10.8 g (0.11 mole) of potassium acetate was used in place of sodium acetate. The yield was 29.0 g (67.8% yield on L-phenylalanine methyl ester hydrochloride). The crystals obtained were analyzed by high performance liquid chromatography to give a ratio of α-isomer:β-isomer of 99.1:0.9.

Example 9

The same procedures as described in Example 1 were carried out except that 8.5 g (0.06 mole) of magnesium acetate was used in place of sodium acetate. The yield was 21.3 g (66.1% yield on L-phenylalanine methyl ester hydrochloride).

The crystals obtained were analyzed by high performance liquid chromatography to give a ratio of α-isomer:β-isomer of 98.8:1.2.

Example 10

The same procedures as described in Example 2 were carried out except that the organic solvents illustrated in Table 2 were used. The results are shown in Table 2.

TABLE 2

| | | α-L-Aspartyl-L-phenylalanine methyl ester | |
|---|---|---|---|
| Experiment No. | Organic Solvent | Yield (%) | % Yield on L-phenylalanine methyl ester hydrochloride |
| 1 | Butyl acetate | 29.0 | 67.8 |
| 2 | Toluene | 29.3 | 68.5 |
| 3 | Ethylene chloride | 29.0 | 67.8 |

Example 11

In 63.3 g of acetic acid, 21.1 g (0.1 mole) of N-trifluoroacetyl-L-aspartic anhydride was suspended and 9.2 g (0.11 mole) of sodium acetate was added at 10°–15° C. with stirring. Successively 21.6 g (0.1 mole) of L-phenylalanine methyl ester hydrochloride was added at the same temperature. The reaction was carried out for 2 hours with stirring at the same temperature.

Precipitated crystals were filtered, washed and dried. Crystals of N-trifluoroacetyl-α-L-aspartyl-L-phenylalanine methyl ester were obtained. The yield was 31.2 g (80.0% yield on L-phenylalanine methyl ester hydrochloride). The crystals obtained were analyzed by high performance liquid chromatography to find α-isomer alone.

Melting point: 150°–151° C.

| Elementary analysis (%) $C_{16}H_{17}N_2O_6F_3$ | | | | |
|---|---|---|---|---|
| | C | H | N | F |
| Found | 49.10 | 4.45 | 7.17 | 14.56 |
| Calculated | 49.24 | 4.39 | 7.18 | 14.60 |

Example 12

The same procedures as described in Example 11 were carried out except that organic carboxylic acid and organic carboxylic acid salt were used as illustrated in Table 3. The results are shown in Table 3.

TABLE 3

| Experiment No. | Organic carboxylic acid | Organic carboxylic acid salt | Yield (g) | Yield (%) |
|---|---|---|---|---|
| 1 | Formic acid | Sodium acetate | 29.3 | 75.1 |
| 2 | Propionic acid | Sodium acetate | 28.9 | 74.1 |
| 3 | Acetic acid | Potassium acetate | 30.0 | 77.0 |
| 4 | Acetic acid | Lithium acetate | 30.5 | 78.2 |
| 5 | Formic acid | Potassium acetate | 29.2 | 74.9 |
| 6 | Propionic acid | Potassium acetate | 28.7 | 73.7 |

Example 13

In 100.4 g of acetic acid, 25.1 g (0.1 mole) of N-benzyloxycarbonyl-L-aspartic anhydride was suspended and 9.2 g (0.11 mole) of sodium acetate was added at 10°–15° C. with stirring. Successively 21.6 g (0.1 mole) of L-phenylalanine methyl ester hydrochloride was added at the same temperature. The reaction was carried out for 4 hours with stirring at the same temperature. Thereafter 75.3 g of water was added at the same temperature and cooled to 0°–5° C. Precipitated crystals were filtered, washed and dried. Crystals of N-benzyloxycarboxnyl-α-L-aspartyl-L-phenylalanine methyl ester were obtained. The yield was 31.2 g (72.9% yield on L-phenylalanine methyl ester hydrochloride).

Melting point: 123.8°–124.8° C.

| Elementary analysis (%) $C_{22}H_{23}N_2O_7$ | | | |
|---|---|---|---|
| | C | H | N |
| Found | 61.58 | 5.70 | 6.53 |
| Calculated | 61.68 | 5.65 | 6.54 |

Example 14

In 28.6 g of acetic acid, 14.3 g (0.1 mole) of N-formyl-L aspartic anhydride was suspended and 9.2 g (0.11 mole) of sodium acetate was added with stirring at 5°–10° C. Successively 21.6 g (0.1 mole) of L-phenylalanine methylester hydrochloride was added and the reaction was carried out for 5 hours with stirring at the same temperature. The reaction mixture was then concentrated and 57.2 g of water was added. Precipitated crystals were filtered, washed and dried. Crystals of N-formyl-α-L-aspartyl-L-phenylalanine methyl ester thus obtained were 30.6 g.

The crystals were analyzed by high performance liquid chromatography to give a ratio of α-isomer:β-isomer of 81.0:19.0. The crystals were purified with a conventional method to give high purity crystals of N-formyl-α-L-aspartyl-L-phenylalanine methyl ester. The yield was 22.3 g (69.3% yield on L-phenylalanine methyl ester hydrochloride).

Melting point: 123.5°–124° C.

| Elementary analysis (%) $C_{15}H_{18}N_2O_6$ | | | |
|---|---|---|---|
| | C | H | N |
| Found | 55.85 | 5.69 | 8.66 |
| Calculated | 55.90 | 5.63 | 8.69 |

Example 15

In 75.3 g of acetic acid, 25.1 g (0.1 mole) of N-benzyloxycarbonyl-L-aspartic anhydride was suspended and 9.2 g (0.11 mole) of sodium acetate was added at 20°–25° C. with stirring. After cooling to 15°–20° C., 64.8 g of an acetic acid solution containing 21.6 g (0.1 mole) of L-phenylalanine methyl ester hydrochloride was added at the same temperature. The reaction was carried out for 2 hours with stirring at the same temperature. Thereafter 110.1 g of water was added at the same temperature and cooled to 0°–5° C. Precipitated crystals were filtered, washed and dried. Crystals of N-benzyloxycarbonyl-α-L-aspartyl-L-phenylalanine methyl ester were obtained. The yield was 29.5 g (68.9% yield on L-phenylalanine methyl ester hydrochloride).

Melting point: 123.8°–124.9° C.

Example 16

The same procedures as described in Example 11 were carried out except that 22.7 g (0.1 mole) of L-phenylalanine methyl ester sulfate was used in place of L-phenylalanine methyl ester hydrochloride and the amount of sodium acetate was increased to 17.6 g (0.21 mole).

Crystals of N-trifluoroacetyl-α-L-aspartyl-L-phenylalanine methyl ester were obtained in the yield of 31.1 g (79.7% yield on L-phenylalanine methyl ester hydrochloride).

Melting point: 150°–151° C.

Example 17

In 100.4 g of acetic acid, 25.1 g (0.1 mole) of N-benzyloxycarbonyl-L-aspartic anhydride was suspended and 21.6 g (0.1 mole) of L-phenylalanine methyl ester hydrochloride was added at 10°–15° C. Successively 9.2 g (0.11 mole) of sodium acetate was added over 30 minutes at the same temperature. The reaction was carried out for 3 hours with stirring at the same temperature. Thereafter 75.3 g of water was added and cooled to 0°–5° C. Precipitated crystals were filtered, washed and dried. Crystals of N-benzyloxycarbonyl-α-L-aspartyl-L-phenylalanine methyl ester were obtained. The yield was 30.0 g (70.1% yield on L-phenylalanine methyl ester hydrochloride).

Melting point: 123°–124° C.

Example 18

In 100.4 g of acetic acid, 25.1 g (0.1 mole) of N-benzyloxycarbonyl-L-aspartic anhydride was suspended and 27.7 g (0.1 mole) of L-phenylalanine methyl ester sulfate was added at 10°–15° C. Successively 11.1 g (0.105 mole) of sodium carbonate was added at the same temperature. The reaction was carried out for 4 hours with stirring at the same temperature. Thereafter 75.3 g of water was added and cooled to 0°–5° C. Precipitated crystals were filtered, washed and dried. Crystals of N-benzyloxycarbonyl-α-L-aspartyl-L-phenylalanine methyl ester were obtained. The yield was 29.9 g (69.9% yield on L-phenylalanine methyl ester sulfate).

Melting point: 123°–124° C.

Example 19

The same procedures as described in Example 18 were carried out except that 4.8 g (0.12 mol) of magnesium oxide is used in place of 11.1 g (0.105 mole) of sodium carbonate.

The yield was 26.0 g (60.7% yield on L-phenylalanine methyl ester sulfate).

Melting point: 123.5°-124.5° C.

Example 20

In 63.3 g of acetic acid, 22.9 g (0.1 mole) of N-trifluoroacetyl-L-aspartic acid was suspended and 10.2 g (0.1 mole) of acetic anhydride was added. The mixture was warmed to 55°-60° C. and stirred for 6 hours at the same temperature. After finishing the reaction, the resulting mixture was cooled to 15°-20° C. and then 9.2 g (0.11 mole) of sodium acetate and 20.5 g (0.095 mole) of L-phenylalanine methyl ester hydrochloride were successively added at the same temperature. The reaction was carried out for 2 hours with stirring at the same temperature. Precipitated crystals were filtered, washed and dried. Crystals of N-trifluoroacetyl-α-L-aspartyl-L-phenylalanine methyl ester were obtained in the yield of 29.3 g (79.0% yield on L-phenylalanine methyl ester hydrochloride). The crystals thus obtained were analyzed by high performance liquid chromatography to find α-isomer alone.

Melting point: 150°-151° C.

| Elementary analysis (%) $C_{16}H_{17}N_2O_6F_3$ | | | | |
| --- | --- | --- | --- | --- |
| | C | H | N | F |
| Found | 49.10 | 4.45 | 7.17 | 14.56 |
| calculated | 49.24 | 4.39 | 7.18 | 14.60 |

Example 21

The same procedures as described in Example 20 were carried out except that organic carboxylic acids and organic carboxylic acid salts were used as illustrated in Table 4. The results are shown in Table 4.

Example 22

The same procedures as described in Example 20 were carried out except that the amount of acetic anhydride was changed to 9.7 g (0.095 mole).

The yield was 29.0 g (78.2% yield on L-phenylalanine methyl ester hydrochloride).

TABLE 4

| Experiment No. | Organic carboxylic acid | Organic carboxylic acid salt | Yield (g) | Yield (%) |
| --- | --- | --- | --- | --- |
| 1 | Formic acid | Sodium acetate | 26.0 | 70.1 |
| 2 | Propionic acid | Sodium acetate | 27.1 | 73.1 |
| 3 | Acetic acid | Potassium acetate | 28.2 | 76.1 |
| 4 | Acetic acid | Lithium acetate | 28.0 | 75.5 |
| 5 | Formic acid | Potassium acetate | 26.1 | 70.4 |
| 6 | Propionic acid | Potassium acetate | 27.3 | 73.6 |

Example 23

In 95.5 g of acetic acid, 26.7 g (0.1 mole) of N-benzyloxycarbonyl-L-aspartic acid was suspended and 10.2 g (0.1 mole) of acetic anhydride was added. The mixture was warmed to 55°-60° C. and stirred for 5 hours at the same temperature. After finishing the reaction, the resulting mixture was cooled to 15°-20° C. and then 9.2 g (0.11 mole) of sodium acetate and 20.5 g (0.095 mole) of L-phenylalanine methyl ester hydrochloride were successively added at the same temperature. The reaction was carried out for 4 hours with stirring at the same temperature. Thereafter 75.3 g of water was added and the mixture was cooled to 0°-5° C. Precipitated crystals were filtered, washed and dried.

The crystals thus obtained were 28.9 g (71.0% yield on L-phenylalanine methyl ester hydrochloride).

Melting point: 123.9°-124.8° C.

Results of elementary analysis were coincided with N-benzyloxycarbonyl-α-L-aspartyl-L-phenylalanine methyl ester.

| Elementary analysis (%) $C_{22}H_{24}N_2O_7$ | | | |
| --- | --- | --- | --- |
| | C | H | N |
| Found | 61.78 | 5.68 | 6.53 |
| Calculated | 61.68 | 5.65 | 6.54 |

Example 24

The same procedures as described in Example 23 were carried out except that 26.3 g (0.095 mole) of L-phenylalanine methyl ester sulfate and 16.8 g (0.21 mole) of sodium acetate were used.

The yield was 27.8 g (68.3% yield on L-phenylalanine methyl ester sulfate).

Example 25

The same procedures as described in Example 23 were carried out except that 9.7 g (0.095 mole) of acetic anhydride was used.

The yield was 27.7 g (68.1% yield on L-phenylalanine methyl ester hydrochloride).

Example 26

In 28.6 g of acetic acid, 16.1 g (0.1 mole) of N-formyl L-aspartic acid was suspended and 10.2 g (0.1 mole) of acetic anhydride was added. The mixture was warmed to 50°-55° C. and stirred for 5 hours at the same temperature. After finishing the reaction, the resulting mixture was cooled to 15°-20° C. and then 9.2 g (0.11 mole) of sodium acetate and 20.5 g (0.095 mole) of L-phenylalanine methyl ester hydrochloride were successively added at the same temperature. The reaction was carried out for 4 hours with stirring at the same temperature. The reaction mixture was then concentrated and 57.2 g of water was added and cooled to 10°-15° C. Precipitated crystals were filtered, washed and dried. Crystals of N-formyl-α-L-aspartyl-L-phenylalanine methyl ester thus obtained were 28.2 g. The crystals were analyzed by high performance liquid chromatography to give a ratio of α-isomer:β-isomer of 81.0:19.0. The crystals were purified with a conventional method to give high purity crystals of N-formyl-α-L-aspartyl-L-phenylalanine methyl ester. The yield was 20.8 g (68.0% yield on L-phenylalanine methyl ester hydrochloride).

Results of elementary analysis were coincided with N-formyl-α-L-aspartyl-L-phenylalanine methyl ester.

| Elementary analysis (%) $C_{15}H_{18}N_2O_6$ | | | |
| --- | --- | --- | --- |
| | C | H | N |
| Found | 55.85 | 5.69 | 8.66 |
| Calculated | 55.90 | 5.63 | 8.69 |

Example 27

The same procedures as described in Example 20 were carried out except that 26.3 g (0.095 mole) of L-phenylalanine methyl ester sulfate was used in place of L-phenylalanine methyl ester hydrochloride and sodium acetate was used in an amount of 17.6 g (0.21 mole).

Crystals of N-trifluoroacetyl-α-L-aspartyl-L-phenylalanine methyl ester were obtained.

The yield was 29.0 g (78.2% yield on L-phenylalanine methyl ester sulfate).

Example 28

The same procedures as described in Example 23 were carried out except that, after preparing anhydride of N-benzyloxycarbonyl-L-aspartic acid, L-phenylalanine methyl ester hydrochloride was added and successively sodium acetate was added.

The yield was 30.3 g (74.4% yield on L-phenylalanine methyl ester hydrochloride)

Example 29

In 95.5 g of acetic acid, 26.7 g (0.1 mole) of N-benzyloxycarbonyl-L-aspartic acid was suspended and 10.2 g (0.1 mole) of acetic anhydride was added. The mixture was warmed to 55°–60° C. and stirred for 5 hours at the same temperature. After finishing the reaction, the resulting mixture was cooled to 10°–15° C. and then 20.5 g (0.095 mole) of L-phenylalanine methyl ester hydrochloride and 9.2 g (0.11 mole) of sodium acetate were successively added at the same temperature. The reaction was carried out for 4 hours with stirring at the same temperature. Thereafter 75.3 g of water was added and the mixture was cooled to 0°–5° C. Precipitated crystals were filtered, washed and dried.

The crystals thus obtained were 30.4 g (74.7% yield on L-phenylalanine methyl ester hydrochloride).

Example 30

In 100.4 g of acetic acid, 25.1 g (0.1 mole) of N-benzyloxycarbonyl-L-aspartic anhydride was suspended and 9.2 g (0.11 mole) of sodium acetate was added with stirring at 10°–15° C. Successively 21.6 g (0.1 mole) of L-phenylalanine methyl ester hydrochloride was added at the same temperature. The reaction was carried out for 4 hours with stirring at the same temperature. Thereafter 87.1 g of water was added to the reaction mixture to adjust the concentration of organic carboxylic acid to 53.5% by weight. After cooling the mixture to 0°–5° C., precipitated crystals were filtered, washed and dried.

The yield of the crystals was 31.0 g (72.4% yield on L-phenylalanine methyl ester hydrochloride).

The crystals were analyzed by high performance liquid chromatography to find α-isomer alone.

Melting point: 123.8°–124.9° C.

| Elementary analysis (%) $C_{22}H_{24}N_2O_7$ | | | |
|---|---|---|---|
| | C | H | N |
| Found | 61.56 | 5.70 | 6.53 |
| Calculated | 61.68 | 5.65 | 6.54 |

Example 31

The same procedures as described in Example 30 were carried out except that organic carboxylic acids and organic carboxylic acid salts were used as illustrated in Table 5. The results are shown in Table 5.

TABLE 5

| Experiment No. | Organic carboxylic acid | Organic carboxylic acid salt | Yield (g) | Yield (%) |
|---|---|---|---|---|
| 1 | Formic acid | Sodium acetate | 30.0 | 70.1 |
| 2 | Propionic acid | Sodium acetate | 30.7 | 71.7 |
| 3 | Acetic acid | Potassium acetate | 31.1 | 72.7 |
| 4 | Acetic acid | Lithium acetate | 30.9 | 72.2 |
| 5 | Formic acid | Potassium acetate | 30.1 | 70.3 |
| 6 | Propionic acid | Potassium acetate | 30.6 | 71.5 |

Example 32

In 100.4 g of acetic acid, 25.1 g (0.1 mole) of N-benzyloxycarbonyl-L-aspartic anhydride was suspended and 9.2 g (0.11 mole) of sodium acetate was added with stirring at 10°–15° C. Successively 21.6 g (0.1 mole) of L-phenylalanine methyl ester hydrochloride was added at the same temperature. The reaction was carried out for 4 hours with stirring at the same temperature. Thereafter 70.9 g of water was added to the reaction mixture to adjust the concentration of organic carboxylic acid to 58.6% by weight. After cooling the mixture to 0°–5° C., precipitated crystals were filtered, washed and dried.

The yield of the crystals was 27.0 g (63.1% yield on L-phenylalanine methyl ester hydrochloride).

The crystals were analyzed by high performance liquid chromatography to find α-isomer alone.

Example 33

In 100.4 g of acetic acid, 25.1 g (0.1 mole) of N-benzyloxycarbonyl-L-aspartic anhydride was suspended and 17.6 g (0.21 mole) of sodium acetate was added with stirring at 10°–15° C. Successively 22.7 g (0.1 mole) of L-phenylalanine methyl ester sulfate was added at the same temperature. The reaction was carried out for 4 hours with stirring at the same temperature. Thereafter 87.1 g water was added to the reaction mixture to adjust the concentration of organic carboxylic acid to 53.3% by weight. After cooling the mixture to 0°–5° C., precipitated crystals were filtered, washed and dried.

The yield of the crystals was 29.5 g (68.9% yield on L-phenylalanine methyl ester sulfate).

Example 34

In 100.4 g of acetic acid, 25.1 g (0.1 mole) of N-benzyloxycarbonyl-L-aspartic anhydride was suspended and 21.6 g (0.1 mole) of L-phenylalanine methyl ester hydrochloride was added with stirring at 5°–10° C. Successively 9.2 g (0.1 mole) of sodium acetate was added at the same temperature. The reaction was carried out for 4 hours with stirring at the same temperature. Thereafter 87.1 g of water was added to the reaction mixture to adjust the concentration of organic carboxylic acid to 53.5% by weight. After cooling to 0°–5° C., precipitated crystals were filtered, washed and dried. Crystals of N-benzyloxycarbonyl-α-L-aspartyl-L-phenylalanine methyl ester were obtained The yield was 31.2 g (72.9% yield on L-phenylalanine methyl ester hydrochloride).

The crystals obtained were analyzed by high performance liquid chromatography to find α-isomer alone.

Example 35

In 100.4 g of acetic acid, 25.1 g (0.1 mole) of N-benzyloxycarbonyl-L-aspartic anhydride was suspended and 22.7 g (0.1 mole) of L-phenylalanine methyl ester sulfate was added with stirring at 5°–10° C. Successively 17.6 g (0.21 mole) of sodium acetate was added at the same temperature. The reaction was carried out for 4 hours with stirring at the same temperature. Thereafter 87.1 g of water was added to the reaction mixture to adjust the concentration of organic carboxylic acid to 53.5% by weight. After cooling to 0°–5° C., precipitated crystals were filtered, washed and dried. Crystals of N-benzyloxycarbonyl-α-L-aspartyl-L-phenylalanine methyl ester were obtained. The yield was 31.2 g (73.1% yield on L-phenylalanine methyl ester sulfate).

The crystals obtained were analyzed by high performance liquid chromatography to find α-isomer alone.

Example 36

In a solvent illustrated in Table 6, 67.0 g (0.25 mole) of N-benzyloxycarbonyl-L-aspartic acid was suspended and acetic anhydride (purity 93%) was added in an amount illustrated in Table 6. The reaction was carried out at 55° C. for 3 hours in the presence of an acid halide shown in Table 6.

Suitable amount of sample was withdrawn from the uniform reaction mixture thus obtained and dissolved in a methanol solution containing 5% by weight of triethylamine. α- and β-Isomers of N-benzyloxycarbonylcarbobenzoxy-L-aspartic acid methyl ester formed by the reaction of N-benzyloxycarbonyl-L-aspartic anhydride with methanol and residual N-benzyloxycarbonyl-L-aspartic acid were determined by high performance liquid chromatography. The content and yield of N-benzyloxycarbonyl-L-aspartic anhydride were calculated from measured values. Results are shown in Table 6.

Comparative Example 1

The same procedures as described in Example 36 were carried out except that acid halides were omitted. The result is illustrated in Table 6.

TABLE 6

| No. | Acid halide (g) | | Acetic anhydride (g) | Solvent (g) | | Yield (%) |
|---|---|---|---|---|---|---|
| Comparative Example-1 | None | | 26.9 | Acetic acid | 129.4 | 42.3 |
| Experiment | | | | | | |
| 1 | $CH_3COCl$ | 0.03 | 26.9 | Acetic acid | 129.4 | 92.5 |
| 2 | $CH_3COCl$ | $6.7 \times 10^{-4}$ | 30.2 | Aceitc acid | | 98.2 |
| 3 | $CH_3CH_2COCl$ | 0.04 | 26.9 | Acetic acid | | 93.0 |
| 4 | $CH_3C_6H_5SO_2Cl$ | 0.04 | 26.9 | Acetic acid | | 93.4 |
| 5 | $CH_3COCl$ | 0.34 | 30.2 | Toluene | 129.4 | 99.3 |
| 6 | $CH_3COBr$ | 0.02 | 26.9 | Acetic acid | 129.4 | 92.6 |
| 7 | $CH_3COCl$ | 0.02 | 26.9 | Acetic acid | | 91.7 |
| 8 | $C_6H_5COCl$ | 0.04 | 26.9 | Acetic acid | | 92.8 |
| 9 | $(CH_2COCl)_2$ | 0.03 | 30.2 | Acetic acid | | 97.9 |
| 10 | trans-ClOCCH=CHCOCl | 0.02 | 27.4 | Acetic acid | | 96.2 |
| 11 | $C_6H_5SO_2Cl$ | 0.03 | 27.4 | Acetic acid | | 97.0 |
| 12 | $CH_3COCl$ | 0.03 | 26.9 | 1,2-Dichloroethane | 129.4 | 94.7 |

Example 37

In a solvent illustrated in Table 7, 67.0 g (0.25 mole) of N-benzyloxycarbonyl-L-aspartic acid was suspended and acetic anhydride (purity 93%) was added in an amount illustrated in Table 7. The reaction was carried out at 55° C. for 3 hours in the presence of an phosphorus halide shown in Table 7.

Suitable amount of sample was withdrawn from the uniform reaction mixture thus obtained and dissolved in a methanol solution containing 5% by weight of triethylamine. α- and β-Isomers of N-benzyloxycarbonylcarbobenzoxy-L-aspartic acid methyl ester formed by the reaction of N-benzyloxycarbonyl-L-aspartic anhydride with methanol and residual N-benzyloxycarbonyl-L-aspartic acid were determined by high performance liquid chromatography. The content and yield of N-benzyloxycarbonyl-L-aspartic anhydride were calculated from measured values. Results are shown in Table 7.

Comparative Example 2

The same procedures as described in Example 37 were carried out except that phosphorus halide were omitted. The result is illustrated in Table 7.

TABLE 7

| No. | Phosphorus halide (g) | | Acetic anhydride (g) | Solvent (g) | | Yield (g) |
|---|---|---|---|---|---|---|
| Comparative Example-2 | None | | | Acetic acid | 129.4 | 42.3 |
| Experiment | | | | | | |
| 1 | $PCl_3$ | 0.027 | 26.9 | Acetic acid | 129.4 | 91.2 |
| 2 | $PBr_3$ | 0.027 | 26.9 | Aceitc acid | | 92.2 |
| 3 | $PCl_3$ | 0.225 | 26.9 | Acetic acid | | 96.4 |
| 4 | $PCl_3$ | 0.027 | 26.9 | Toluene | 129.4 | 92.6 |
| 5 | $PBr_3$ | 0.027 | 26.9 | Toluene | | 95.8 |
| 6 | $PCl_5$ | 0.013 | 26.9 | Toluene | | 97.2 |
| 7 | $PBr_3$ | 0.013 | 26.9 | Acetic acid | 129.4 | 94.1 |
| 8 | $PCl_5$ | 0.013 | 26.9 | Acetic acid | | 93.7 |
| 9 | $PCl_3$ | $6.7 \times 10^{-4}$ | 30.2 | Acetic acid | | 98.1 |
| 10 | $PCl_3$ | 0.027 | 30.2 | 1,2-Dichloroethane | 129.4 | 98.5 |
| 11 | $PBr_3$ | 0.027 | 26.9 | 1,2-Dichloroethane | | 93.9 |
| Experiment | Acid halide (g) | | | | | |

TABLE 7-continued

| No. | | Acetic anhydride (g) | Solvent (g) | | Yield (g) |
|---|---|---|---|---|---|
| 13 | $C_6H_5COCl$ | 0.04 | 1,2-Dichloroethane | 129.4 | 97.8 |
| 14 | p-$CH_3C_6H_5SO_2Cl$ | 0.03 | 1,2-Dichloroethane | | 98.1 |
| 15 | $(CH_3)_3CCOCl$ | 0.03 | Acetic acid | 129.4 | 92.0 |
| 16 | $SO_2Cl_2$ | 0.03 | Acetic acid | | 91.7 |
| 17 | $SOCl_2$ | 0.03 | Acetic acid | | 92.4 |
| 18 | $C_6H_5CH_2OCOCl$ | 0.03 | Acetic acid | | 91.8 |
| 19 | $CH_3CH_2SO_2Cl$ | 0.03 | Acetic acid | | 92.2 |
| 20 | $POCl_3$ | 0.03 | Acetic acid | | 92.5 |
| 21 | $SOCl_2$ | 0.03 | Acetic acid | | 98.7 |

Example 38

In 240 g of tetrahydrofuran, 26.7 g (0.1 mole) of N-benzyloxycarbonyl-L-aspartic acid was dissolved. Reaction was carried out at 55° C. for 5 hours by bubbling phosgene into the solution at a rate of 5 g/hr. Dry nitrogen gas was blown through the reaction mixture after finishing the reaction to remove residual phosgene. Tetrahydrofuran was successively removed under reduced pressure. After drying at room temperature under reduced pressure, 26.0 g of crystals was obtained.

Infrared spectrum of the crystals were coincided with N-benzyloxycarbonyl-L-aspartic anhydride.

Purity of the crystals determined by high performance liquid chromatography was 93.0%. The yield was 97.0%.

Example 39

In 240 g of toluene, 16.1 g (0.1 mole) of N-formyl-L-aspartic acid was suspended. Reaction was carried out at 50° C. for 10 hours by bubbling phosgene into the solution at a rate of 5 g/hr. Dry nitrogen gas was blown through the reaction mixture after finishing the reaction to remove residual phosgene. Precipitated crystals were filtered and dried. Crystals thus obtained were 13.1 g.

Infrared spectrum of the crystals were coincided with N-formyl-L-aspartic anhydride.

Purity of the crystals determined by high performance liquid chromatography was 96.0%. The yield was 87.9%.

Example 40

In 240 g of tetrahydrofuran, 23.3 g (0.1 mole) of N-tert-butoxycarbonyl-L-aspartic acid was dissolved. Reaction was carried out at 10° C. for 10 hours by bubbling phosgene into the solution at a rate of 5 g/hr. Dry nitrogen gas was blown through the reaction mixture after finishing the reaction to remove residual phosgene. After finishing the reaction, the same procedures as described in Example 38 were carried out. Crystals thus obtained were 23.0 g.

Infrared spectrum of the crystals were coincided with N-tert-butoxycarbonyl-L-aspartic anhydride.

Purity of the crystals determined by high performance liquid chromatography was 91.5%. The yield was 97.9%.

Example 41

In 240 g of tetrahydrofuran, 37.5 g (0.1 mole) of N-trityl-L-aspartic acid was dissolved. Reaction was carried out at 10° C. for 5 hours by bubbling phosgene into the solution at a rate of 5 g/hr. Dry nitrogen gas was blown through the reaction mixture after finishing the reaction to remove residual phosgene. Tetrahydrofuran was successively removed under reduced pressure After drying at room temperature under reduced pressure, 36.7 g of crystals was obtained.

Purity of the crystals was determined by high performance liquid chromatography was 96.3%. The yield was 99.0%.

Examples 42-44

In 240 g of each solvent illustrated in Table 8, 26.7 g (0.1 mole) of N-benzyloxycarbonyl-L-aspartic acid was dissolved or suspended. The same reaction and isolation procedures as described in Example 38 were carried out. The results are shown in Table 8.

TABLE 8

| Example | Solvent | Reaction temperature (°C.) | Reaction time (hr) | Yield (%) |
|---|---|---|---|---|
| 42 | Toluene | 55 | 10 | 96.7 |
| 43 | 1,2-Dichloroethane | 55 | 10 | 98.9 |
| 44 | Ethyl acetate | 10 | 10 | 89.3 |

Example 45

In 240 g of tetrahydrofuran, 26.7 g (0.1 mole) of N-benzyloxycarbonyl-L-aspartic acid was dissolved and 0.2 g of anhydrous magnesium chloride was added. Reaction was carried out at 50° C. for 2 hours by bubbling phosgene into the solution at a rate of 5 g/hr. Dry nitrogen gas was blown through the reaction mixture after finishing the reaction to remove residual phosgene. Tetrahydrofuran was successively removed under reduced pressure. After drying at room temperature under reduced pressure, 25.8 g of crystals was obtained.

Infrared spectrum of the crystals were coincided with N-benzyloxycarbonyl-L-aspartic anhydride.

Purity of the crystals determined by high performance liquid chromatography was 96.7%. The yield was 100%.

Examples 46-57

The same reaction and isolation procedures as described in Example 45 were carried out by using various N-protecting groups, metal compound additives and solvents as illustrated in Table 9. Results are summarized in Table 9.

TABLE 9

| Example | N-Protecting group | Metal compound | Solvent | Reaction temperature (°C.) | Reaction time (hr) | Yield (%) |
|---|---|---|---|---|---|---|
| 46 | Benzyloxycarbonyl | LiCl | Tetrahydrofuran | 50 | 2 | 91.1 |

TABLE 9-continued

| Example | N-Protecting group | Metal compound | Solvent | Reaction temperature (°C.) | Reaction time (hr) | Yield (%) |
|---|---|---|---|---|---|---|
| 47 | Benzyloxycarbonyl | NaOH | Tetrahydrofuran | 50 | 2 | 92.3 |
| 48 | Benzyloxycarbonyl | K$_2$CO$_3$ | Tetrahydrofuran | 50 | 2 | 91.4 |
| 49 | Benzyloxycarbonyl | CaCl$_2$ | Tetrahydrofuran | 50 | 2 | 100 |
| 50 | Benzyloxycarbonyl | Zn(OCO$_2$CH$_3$)$_2$ | Toluene | 55 | 2.5 | 90.8 |
| 51 | Benzyloxycarbonyl | AlCl$_3$ | Carbon tetrachloride | 55 | 2.5 | 94.3 |
| 52 | Benzyloxycarbonyl | SnO | Tetrahydrofuran | 50 | 2 | 93.0 |
| 53 | Benzyloxycarbonyl | Fe(OH)$_3$ | Tetrahydrofuran | 50 | 2 | 97.2 |
| 54 | Formyl | MgCl$_2$ | Toluene | 55 | 2.5 | 96.0 |
| 55 | Formyl | LiCl | Ethyl acetate | 10 | 4 | 94.3 |
| 56 | tert-Butoxycarbonyl | CaCl$_2$ | Tetrahydrofuran | 10 | 4 | 87.9 |
| 57 | Trityl | Na$_2$CO$_3$ | Tetrahydrofuran | 10 | 4 | 85.4 |

Comparative Examples 3-5

In 240 g of tetrahydrofuran or toluene, 26.7 g (0.1 mole) of N-benzyloxycarbonyl-L-aspartic acid was dissolved. The reaction was carried out at the temperatures illustrated in Table 10 in the absence of metal compounds by bubbling phosgene into the solution at the rate of 5 g/hr. The same procedures as described in Example 45 were carried out for isolating the product.

The results are shown in Table 10. In any cases, the yield was 50-60%.

TABLE 10

| Comparative Example | Solvent | Reaction temperature (°C.) | Reaction time (hr) | Yield (%) |
|---|---|---|---|---|
| 3 | Tetrahydrofuran | 50 | 2 | 57.3 |
| 4 | Tetrahydrofuran | 10 | 4 | 58.1 |
| 5 | Toluene | 55 | 2.5 | 52.0 |

The following examples show that the presence of water negatively affects the reaction, that the presence of acetic acid beneficially affects the reaction and that acetic acid is not an inert solvent when used in conjunction with a base, but instead plays an important role in results obtained in the reaction.

Example 58 (present invention)

To 24.9 g (0.1 mole) of N-benzyloxycarbonyl-L-aspartic acid anhydride in 100.4 g of acetic acid were added 21.6 g (0.1 mole) of L-phenylalanine methyl ester hydrochloride and 7.6 g (0.055 mole) of potassium carbonate. The reaction was carried out for 3 hours with stirring at 15°-20.C. Thereafter 75.3 g of water was added and the mixture was stirred for one hour at 15°-20.C. The precipitated crystals were filtered, washed and dried to obtain crystals of N-benzyloxycarbonyl-α-L-aspartyl-phenylalanine methyl ester. Analysis of HPLC revealed that the crystals had an α-isomer:β-isomer ratio of 99.6:0.4. The yield of the α-isomer was 28.6 g. In the filtrate, 7.2 g of the α-isomer and 6.2 g of the β-isomer were present.

The total yield of the α-isomer as 35.8 g (83.3% based on the N-benzyloxycarbonyl-L-aspartic acid anhydride).

Comparative Example 58a

This example illustrates substituting an inert solvent for acetic acid as the reaction solvent.

To 24.9 g (0.1 mole) of N-benzyloxycarbonyl-L-aspartic acid anhydride in 100.4 g of ethyl acetate were added 21.6 g (0.1 mole) of L-phenylalanine methyl ester hydrochloride and 7.6 g (0.055 mole) of potassium carbonate. The reaction was carried out for 3 hours with stirring at 15°-20.C.

Analysis of HPLC revealed that the yield of the α-isomer in the reaction mixture was 0.52 g (1.2% based on the N-benzyloxycarbonyl-L-aspartic acid anhydride).

In this example, virtually no desired produced was obtained because L-phenylalanine methyl ester hydrochloride and potassium carbonate do not dissolve in ethyl acetate. No water was added to the reaction mixture after the reaction because, when the water is added, two layers of liquid form and no precipitation occurs. Thus, there is no advantage in adding water to the reaction product for the purpose of obtaining crystals of N-benzyloxycarbonyl-α-L-phenylalanine methyl ester when ethyl acetate is used as the reaction solvent instead of acetic acid.

Comparative Example 58b

This example illustrates the adverse effect of substituting an inert solvent for acetic acid as the reaction solvent, even in the presence of water.

To 24.9 g (0.1 mole) of N-benzyloxycarbonyl-L-aspartic acid anhydride in 100.4 g of ethyl acetate were added 21.6 g (0.1 mole) of L-phenylalanine methyl ester hydrochloride and 7.6 g (0.055 mole) of potassium carbonate dissolved in 9.3 g of water. The reaction was carried out for 3 hours with stirring at 15°-20 C. Thereafter, 100.4 g of acetic acid and 75.3 g of water was added to the concentrate and the mixture was stirred for one hour at 15°-20.C. Precipitated crystals were filtered, washed and dried to obtain crystals of N-benzyloxycarbonyl-α-L-aspartyl-L-phenylalanine methyl ester.

Analysis of HPLC revealed that the crystals had an α-isomer:β-isomer ratio of 99.5:0.5. The yield of the α-isomer was 20.6 g. In the filtrate, 8.4 g of the α-isomer and 9.5 g of the β-isomer were present.

The total yield of the α-isomer was 29.0 g (67.5% base on the N-benzyloxycarbonyl-L-aspartic acid anhydride).

Because the potassium carbonate was dissolved in 9.3 g of water, the reaction proceeds without problem. However, the yield of desired product is inferior to the yield obtained in Example 58. Higher yields of desired product can only be obtained by the economically undesirable expedient employing a higher mole ratio of L-phenylalanine methyl ester hydrochloride to N-benzyloxycarbonyl-L-aspartic acid anhydride. After the reaction, the solvent (ethyl acetate) was distilled off by concentrating the reaction mixture under reduced pressure in order to prevent the reaction mixture from separating into two layers when water is added to precipitate crystals. In the precipitation procedure, acetic acid was used together with water so that the isolation procedure would be carried out under the same conditions as in Example 58.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the preparation of an N-protected α-L-aspartyl-L-phenylalanine methyl ester from an N-protected L-aspartic anhydride and L-phenylalanine methyl ester in a non-aqueous organic solvent, the improvement which comprises employing the L-phenylalanine methyl ester in the form of a mineral acid salt thereof and conducting the reaction in the presence of either (a) a salt of an organic carboxylic acid or, when the nonaqueous organic solvent comprises an organic carboxylic acid, at least one member of the group consisting of (i) an alkali metal inorganic base, (ii) an alkaline earth metal inorganic base, (iii) an ammonium, alkali metal or alkaline earth metal salt of an organic carboxylic acid and (iv) ammonium carbonate.

2. The process of claim 1 wherein the N-protected L-aspartic anhydride is reacted with a mineral acid salt of L-phenylalanine methyl ester in an inert organic solvent in the presence of a salt of an organic carboxylic acid.

3. The process of claim 2, wherein the N-protected L-aspartic anhydride is N-benzyloxycarbonyl aspartic anhydride.

4. The process of claim 2, wherein the mineral acid salt is the hydrochloride.

5. The process of claim 2, wherein the salt of an organic carboxylic acid is sodium acetate.

6. The process of claim 2, wherein the salt of the organic acid is added to a suspension of the reactants in the organic solvent.

7. The process of claim 1, wherein the N-protected L-aspartic anhydride is reacted with a mineral acid salt of L-phenylalanine methyl ester in a solvent comprising an organic carboxylic acid and in the presence of an alkali metal or an alkaline earth metal organic base, an ammonium, alkali metal or an alkaline earth metal salt of an organic carboxylic acid or ammonium carbonate.

8. The process of claim 7, wherein the N-protected L-aspartic anhydride is N-benzyloxycarbonyl aspartic anhydride.

9. The process of claim 7, wherein the mineral acid salt is the hydrochloride.

10. The process of claim 7, wherein the organic carboxylic acid is acetic acid.

11. The process of claim 7, wherein the acetic acid is the sole reaction solvent.

12. The process of claim 1, wherein the reaction is conducted in the presence of an alkali metal salt of a lower fatty acid.

13. The process of claim 12, wherein the N-protected L-aspartic anhydride is N-benzyloxycarbonyl-L-aspartic anhydride.

14. The process of claim 13, wherein the N-benzyloxycarbonyl-α-L-aspartyl-L-phenylalanine methyl ester is selectively crystallized from the reaction mixture by the addition of water thereto after the reaction is finished.

15. The process of claim 1, wherein the starting N-protected L-aspartic anhydride is produced by reacting the corresponding N-protected L-aspartic acid with acetic anhydride in an organic carboxylic acid in the presence of an acid halide or a phosphorus halide.

16. The process of claim 15, wherein the acid halide or phosphorous halide is $CH_3COCl$, $PCl_3$ or $SOCl_2$.

17. The process of claim 15, wherein the N-protected L-aspartic acid is N-benzyloxycarbonyl-L-aspartic acid.

18. The process of claim 1, wherein the N-protected L-aspartic anhydride is produced by reacting the corresponding N-protected L-aspartic acid with phosgene in an organic solvent.

19. The process of claim 18, wherein the reaction with phosgene is conducted in the presence of an oxide, hydroxide or a salt of an alkali metal or an alkaline earth metal.

20. A process for the production of N-benzyloxycarbonyl-α-L-aspartyl-L-phenylalanine methyl ether in crystalline form in high purity which comprises the steps of (a) reacting N-benzyloxycarbonyl-α-L-aspartic acid with acetic anhydride in acetic acid and, without isolation thereof, (b) reacting the thus-produced N-benzyloxycarbonyl-α-aspartic acid anhydride in the acetic acid in which it was produced with L-phenylalanine methyl ester hydrochloride in the presence of sodium acetate, and then (c) adding water to the acetic acid solution of the reaction product to a 45 to 70% by weight acid concentration to precipitate the thus-produced N-benzoyloxycarbonyl-α-L-phenylalanine methyl ester in crystalline form therefrom.

* * * * *